United States Patent [19]

Weckstrom

[11] Patent Number: 5,570,179
[45] Date of Patent: Oct. 29, 1996

[54] MEASURING SENSOR AND MEASURING ARRANGEMENT FOR USE IN THE ANALYSIS OF GAS MIXTURES

[75] Inventor: Kurt Weckstrom, Espoo, Finland

[73] Assignee: Instrumentarium Oy, Finland

[21] Appl. No.: 358,071

[22] Filed: Dec. 15, 1994

[30] Foreign Application Priority Data

Dec. 16, 1993 [FI] Finland ................................ 935682

[51] Int. Cl.$^6$ ............................................. G01N 21/69
[52] U.S. Cl. ........................ 356/311; 356/316; 356/417
[58] Field of Search .................................... 356/311, 316, 356/417

[56] References Cited

U.S. PATENT DOCUMENTS

| | | |
|---|---|---|
| 2,943,223 | 6/1960 | Fay . |
| 3,032,654 | 5/1962 | Fay et al. ............................ 356/306 |
| 3,336,493 | 8/1967 | Lambert . |
| 4,233,513 | 11/1980 | Elder et al. . |
| 4,633,705 | 1/1987 | Meriläinen et al. . |
| 4,898,465 | 2/1990 | Crawford et al. . |
| 5,070,245 | 12/1991 | Rantala et al. . |
| 5,118,989 | 6/1992 | Egermeier et al. . |
| 5,412,467 | 5/1995 | Makczewski et al. ................. 356/316 |

FOREIGN PATENT DOCUMENTS

| | | |
|---|---|---|
| 337933 | 2/1989 | European Pat. Off. . |
| WO93/10438 | 5/1993 | WIPO . |

OTHER PUBLICATIONS

Emission Spectrometric Method and Analyzer for Traces of Nitrogen in Argon, Homer Ray, Paul H. Mohr, and Gerhard A. Cook, Analytical Chemistry, vol. 34, No. 10, Sep. 1962, pp. 1254–1260.

*Primary Examiner*—F. L. Evans
*Attorney, Agent, or Firm*—Andrus, Sceales, Starke & Sawall

[57] ABSTRACT

The invention relates to a measuring sensor for the spectroscopic analysis of gas mixtures by means of a silent electrical discharge. A measuring sensor (1) includes a chamber (4), provided with a wall (16) made of a dielectric material, flow connections (5, 6) in this wall for carrying therethrough a gas mixture to be analyzed into ($G_1$) and out of ($G_2$) the chamber at a pressure (P) equal to that of ambient air, electrodes (2, 3) on the opposite sides of the chamber with a high alternating voltage (U) applied therebetween, and at least one window (8) in this wall, which is transmissive to wavelengths to be measured. In addition, the sensor includes a light detector element (12) for measuring the intensity of a radiation coming through the window. Said high alternating voltage (U) has a frequency which is at least in the order of 10 kHz for generating in a gas mixture (G) a radiation emission based on the non-ionizing excitation of molecules and/or atoms. The measuring arrangement of the invention includes a measuring sensor operating on some other measuring principle, which produces a signal for analyzing at least one other gas component included in the gas mixture by using a computing unit. The measuring values can be output separately or used for checking the analyzing results received from various measuring sensors and, if necessary, for effecting corrections to the results.

29 Claims, 5 Drawing Sheets

MEASURING SENSOR AND MEASURING ARRANGEMENT FOR USE IN THE ANALYSIS OF GAS MIXTURES

The present invention relates to a measuring sensor for the spectroscopic analysis of gas mixtures by means of a silent electrical discharge, the measuring sensor comprising a chamber which includes: a wall made primarily of a dielectric material and surrounding the chamber; through-going flow connections in this wall for passing a gas mixture to be analyzed into and out of the chamber at a pressure approximately equal to that of ambient air; electrodes on the opposite sides of the chamber with a high alternating voltage applied therebetween; and at least one window included in this wall and permeable to wavelengths to be measured; and comprising at least one light detector element positioned for measuring the intensity of radiation emitted through said window. The invention relates also to a measuring arrangement for the analysis of gas mixtures, the measuring arrangement comprising at least: a measuring sensor operating on a spectroscopic first measuring principle and including a light detector element which produces an electrical signal for the radiation emission which is provided by a silent electrical discharge occurring in a gas mixture and produced by a high-voltage electrical field in said gas mixture which is at a pressure approximately equal to that of ambient air and in a certain volume; and a computing unit for the determination of at least a first gas component to be measured at any given time and/or the concentration thereof on the basis of a received electrical signal.

In particular, the invention relates to a sensor and a measuring arrangement for measuring the concentration of such gas components included in gases and gas mixtures which, on the one hand, contain gas components which have no infrared absorption or which cannot be measured paramagnetically or by other passive measuring techniques and which typically contain gas components that are readily dissociated by the action of externally introduced activation energy, such as an electrical field or the like.

The measuring sensor and arrangement are especially applicable for measuring the concentration of nitrogen, helium, argon, xenon and other noble gases included in gas mixtures, such as those used in anesthesia. The measuring sensor and arrangement may also be applicable for measuring the concentrations of hydrogen, chlorine and fluorine.

In gas mixtures, the measurements for the concentrations of gas components are most commonly based on infrared technique, wherein the infrared absorption induced by a gas in permeating radiation is dependent on the number of molecules, i.e. on the concentration of a gas component. The publication U.S. Pat. No. 4,233,513 discloses one measuring arrangement of this type. The method is applied e.g. in patient monitors for measuring carbon dioxide, nitrous oxide or laughing gas, and anesthesia gases. The measuring accuracy and reliability are relatively good but a problem is that all gases of interest do not have infrared absorption. These include all atomic gases, such as noble gases, and all homonuclear diatomic molecules, such as oxygen, nitrogen, hydrogen, chlorine and fluorine.

The measurement of oxygen is generally based on a chemical reaction or on the utilization of a paramagnetic phenomenon. The publication U.S. Pat. No. 4,633,705 describes one measuring sensor, which is applicable for measuring oxygen concentration and based on paramagnetism and which provides a good accuracy and reliability. On the other hand, the measuring techniques based on a chemical phenomenon are too slow for several applications when the measuring speed thereof is compared to the fluctuation rate of variations in a target gas.

Efforts have been made to use the Raman effect for the detection of both nitrogen and oxygen but the scattering effect is extremely weak and, therefore, designing a measuring system that would be sufficiently compact and inexpensive to enable its routine use e.g. in hospitals is not possible at least with presently known technology. The noble gases do not have the Raman scattering and, thus, the measuring thereof has been effected by means of mass spectrometry. However, this device is expensive and bulky and requires a low gas pressure to function and, thus, it is not preferable either e.g. for surgical use in hospitals.

In addition, measuring techniques based on the Raman effect and mass spectrometry are insensitive e.g. to minor concentrations of nitrogen. Gas chromatography can be used for the detection of gas components and for measuring the concentration thereof, but this method is slow and inapplicable to continuous measuring.

It is prior known to analyze gas mixtures and to determine the concentrations of gas components included therein chromatographically and spectroscopically by passing a gas mixture to be examined into a chamber and by subjecting it to an electrical field, and by measuring the intensity of resulting radiation at various wavelengths. This type of gas sensor based on electrical discharge is disclosed e.g. in the publication U.S. Pat. No. 4,898,465. In this measuring sensor, a gas mixture to be examined is maintained at a very low pressure, whereby the action of an electrical field produces a conventional effluvium or glow discharge known and used in many other applications as well. In glow discharge, a major portion and in most cases most of the gas or gases is in the ionized form. Thus, in order to be functional, such a device requires a pressure which is at least less than 0.01 bar and often less than 0.003 bar and taking a sample at such a pressure from a gas flow to be examined and having a pressure of ambient air or higher causes major problems as a continuous process. In addition, a strong ionization also dissociates at least the high molecular gases, such as anesthesia gases, included in a gas mixture, which leads to incorrect measuring results.

Another type of radiation source is described in the publication U.S. Pat. No. 5,118,989. This publication discloses a chamber containing a gas to be examined, wherein the electrodes are located on the same side of the chamber in an overlapping pattern and hence provide a slightly screening radiation source based on surface discharge, in other words, corona discharge. The purpose is to produce an eximer plasma emitting UV radiation. As both electrodes are located on the same side of the chamber, most of the electrical field is produced within an insulation and just a tiny portion in a gas sample. Thus, the excitation power will be poor and it is necessary to use a high voltage and possibly a pressure lower than normal atmospheric pressure. In any case, the purpose is to produce plasma, in other words, a quite strongly ionized gas. Thus, this radiation source has the same drawbacks as the above described sensor.

An ionization cell described in the publication U.S. Pat. No. 3,336,493 and applicable to gas chromatography is intended for producing a high discharge output and luminosity, and for this reason an essential part of the cell structure comprises a cooling system of electrodes. The described solution is hardly applicable to the analysis of gas mixtures containing other than atomic and diatomic gas components as it dissolves the molecules of higher molecular gases. This solution has also the same drawbacks as described above.

Prior known is also a radiation source based on a so-called "silent electrical discharge" or effluvium for use in the spectroscopic analysis of gas mixtures. A device operating on the same principle has also been used as an ozone generator. Such a silent electrical discharge occurs in a gas surrounded by an electrically insulating material at normal atmospheric pressure when the excitation is effected by using a high-voltage, generally mains-frequency 50–60 Hz alternating current. The silent discharge does not work on direct current. The gas excitation is effected in a plurality of micro-discharges and the ozone generator is intended to ionize and dissociate the oxygen as effectively as possible. The publication Analytical Chemistry: vol. 34, No. 10, September 1962, pp. 1254–1260: "Emission Spectrometric Method and Analyzer for Traces of Nitrogen in Argon" describes a measuring sensor for the determination of minor concentrations of nitrogen included as an impurity in an industrially produced argon gas. The same sensor is disclosed also in the publication U.S. Pat. No. 2,943,223. In the sensor described in these two publications, the excitation and discharge of gas molecules is generated in a gas mixture existing at atmospheric pressure and in a glass chamber by means of a high alternating voltage. The alternating voltage is generated by means of a step-up transformer from the mains current having a frequency of 60 Hz and the recommended voltage is 10 kV. It is pointed out in the cited publications that the discharge in argon begins at a voltage of approximately 3 kV and that, at higher voltages of e.g. more than 15 kV, the glass of a chamber begins to deteriorate with local arc discharges occurring in the chamber. The described arrangement is suitable for the analysis of very simple mixtures (argon+nitrogen) of the low molecular gases set forth in the cited publications but not for the analysis of gas mixtures containing a larger number of or higher molecular gas components, since this particular type of electrical field causes dissociation and/or faulty excitation of higher molecular gases. This leads to incorrect measuring results for the concentration of gas components, which cannot be corrected by computation. In addition, the sample chamber operating as a radiation source in the cited publications is long and bulky, as a suitable length for the chamber was considered to be 200–250 mm, a width of 25–50 mm, and an arcing distance of 5 mm. This would result in a minimum chamber capacity of 25 $cm^3$ and a suitable volume flow rate for the gas was considered to be 2.3 l/min, which is far too much for applications with a low volume flow rate and/or in which the concentration measurement can only be effected on a small portion of a targeted volume flow bound for the actual use.

A general object of this invention is to eliminate some of the above-described problems and to provide a compact and inexpensive measuring sensor and measuring arrangement suitable for the identification of gas components included in a gas mixture which is at a substantially normal atmospheric pressure and contains a plurality of and possibly also high molecular gas components as well as for measuring the concentrations thereof, in other words, for the analysis of a gas mixture and its gas components. Thus, a particular object of the invention is to provide such a measuring sensor which would entail no or as little dissociation and ionization of molecules as possible and which is sufficiently high-speed and provides, even at a very low volume flow rate of a gas, e.g. not more than 200 ml/min., either a substantially continuous measuring result or at least in patient monitoring, when synchronized with the respiration of a patient, a real-time measuring result for every respiratory cycle. A further object of the invention is to provide a measuring sensor which is at least principally functional at all such gas mixture pressures which sustain a human activity without auxiliary equipment. An object of the invention is to provide such a measuring sensor and measuring arrangement which is suitable in connection with a gas mixture for the identification and concentration measurement of especially such gas components which do not have a distinct or otherwise useful infrared absorption or some other suitable radiation absorption or the like and which cannot be measured by the utilization of e.g. paramagnetism. Another object of the invention is to provide a measuring sensor which is capable, by using the same measuring chamber, of determining the values of a plurality of components included in a gas mixture for identification and a concentration reading either simultaneously or at very short time intervals. An object of the invention is to provide also a measuring arrangement which is capable, whenever necessary, of correcting the identification and concentration measurement values of gas components obtained by various measuring techniques, including at least spectroscopic analysis by means of a silent gas discharge, infrared-absorption analysis, and paramagnetic analysis. A further object is to provide a device which would be relatively compact in overall size, and as accurate as possible even at low concentrations of gas components to be measured as well as for gas mixtures including a plurality of or complex components. The device should be reliable and have a reasonable price.

The gas to be measured would primarily be nitrogen but also atomic gases, such as helium and argon, may be relevant when the application involves gases for use in anesthesia. Also other corresponding gases should be subjectable to measuring. A closed gas circulation is becoming more and more popular nowadays in connection with patient anesthesia. The lungs will be exhausted of nitrogen gas as laughing gas and anesthesia gases are delivered into the respiratory system along with oxygen. Therefore, the monitoring of nitrogen has become ever more important. Even a slight increase in nitrogen concentration during the course of a surgical operation may for example set an alarm indicating a leak in the system or can result in an air embolism, in other words, air entrapped in the blood stream, which is dangerous to a patient. Thus, an object of the invention is to provide a sensor which has a high sensitivity and accuracy even at low concentrations of nitrogen, for example in the order of 0.1–2%, but which is also capable of measuring higher concentrations approaching 100%. However, with other gases and in other applications, the concentrations of various gas components may of course be entirely different when compared to the above.

The above-described problems can be solved and the above-defined objects are achieved by means of a measuring sensor of the invention, which is characterized by what is set forth in the claims, and by means of a measuring arrangement characterized by what is also set forth in the claims.

The sensor and arrangement of this invention for measuring the components of a gas mixture are principally designed as one component of a patient monitor for measuring the gas mixtures being used. The sensor of the invention is capable of measuring for example nitrogen and noble gases, such as helium and argon, in gas mixtures including a plurality of and also high molecular components. The sensor operates at a normal and at other humanly acceptable pressures and is based on the electrical excitation of molecules of a gas mixture by means of a high-frequency high voltage. Unexpectedly, an electrical field of the invention has been discovered to be such that at least substantial dissociation is avoided and does not occur in gases, such as $CO_2$, $H_2O$ and $N_2O$, possibly present in a gas mixture and being higher molecular gases than diatomic gases and not even in gases, such as halogenated hydrocarbons, which are even higher molecular gases than those mentioned above and which in this application include e.g. halotane, isoflurane, enflurane, sevoflurane, desflurane, ether and trichloroethylene.

The sensor of the invention is at its highest sensitivity when the nitrogen concentration is low and becomes more and more saturated as the nitrogen concentration approaches the less interesting nitrogen concentration of air. Thus, the sensor is particularly well suitable for the very situation set forth as one of the objects. However, the measuring range can be re-adjusted by the appropriate selection of wavelengths to be measured. It is self-evident that this solution can also be used for other applications which require the identification of one or a plurality of gas components or the measuring of concentrations of gas components. Other possible applications could include various products relating to security, such as gas alarms or the like. Even other applications can be found. The sensor is also provided with a measuring chamber which is small in volume or capacity, typically in the order of 0.1 $cm^3$, whereby the gas in said chamber replaces itself even at a very low volume flow at a rapid rate to enable, if necessary, real-time measuring at a frequency which can be five to ten times a second or more.

The invention will now be desribed in more detail with reference to the accompanying drawings, in which FIG. 1A shows one preferred embodiment for a measuring sensor of the invention in a plan view looking in the direction of I in FIG. 1B and provided with one embodiment for a light detector arrangement, including analyzing filters provided with narrow transmission bands.

Figure 1A:
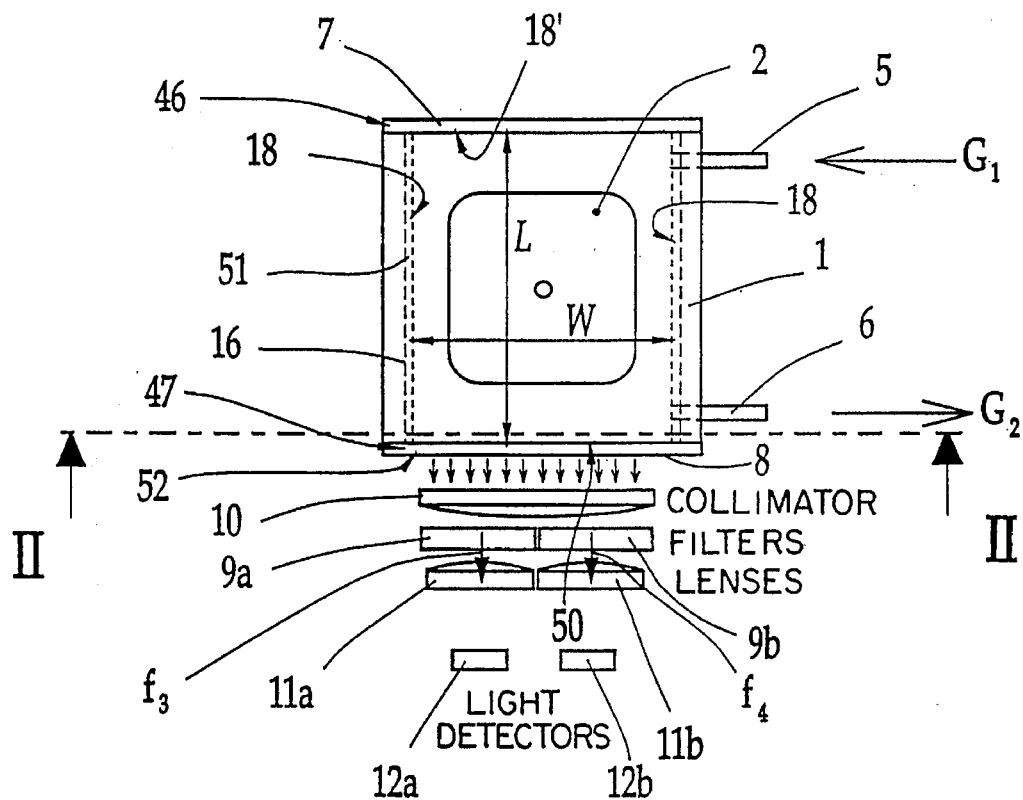
FIG. 1B shows a cross-section of the measuring sensor of FIG. 1A along a line II—II.
Figure 1B:
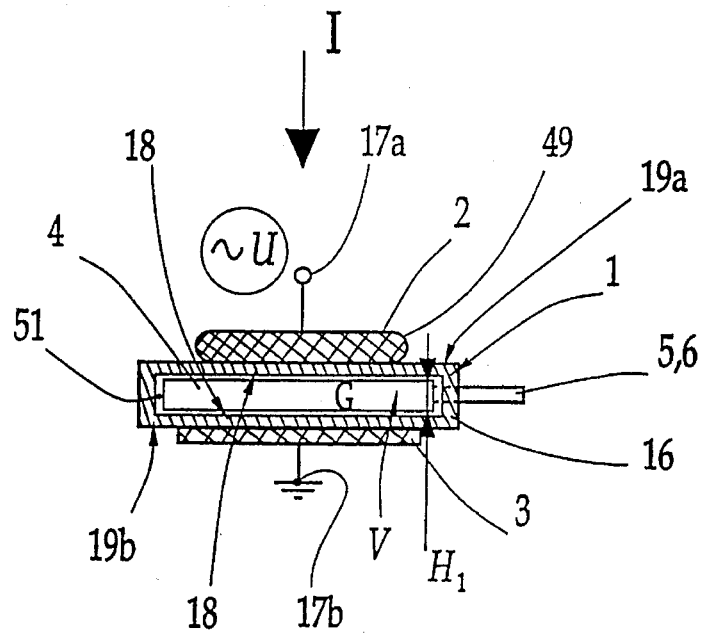
Figure 7:
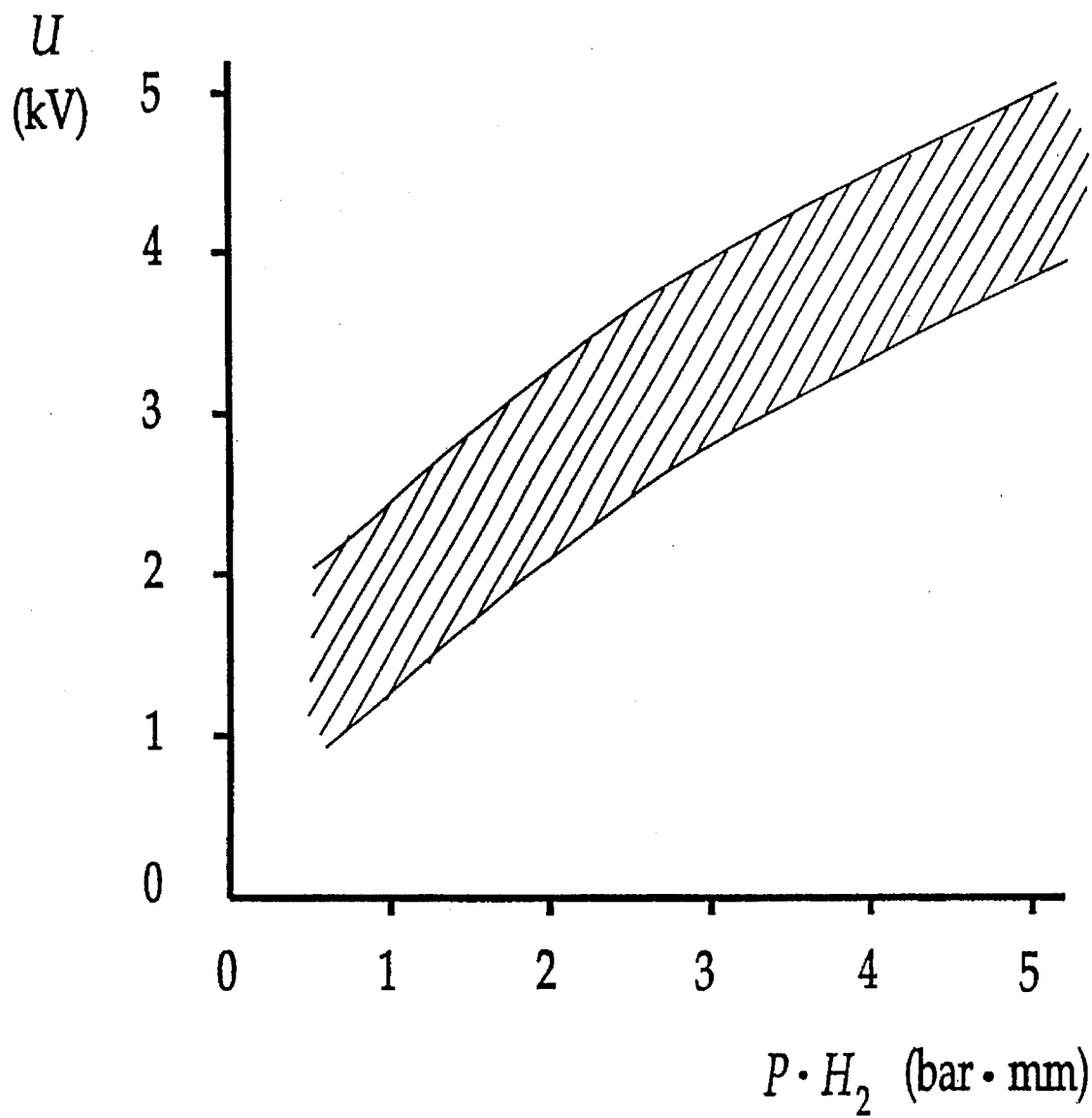
FIG. 7 shows principally the dependence of an excitation voltage on a distance between electrodes and on the gas pressure.

A measuring sensor 1 as shown in FIGS. 1A and 1B includes a wall 16, made of an electrically insulating, i.e. dielectric material and surrounding a measuring chamber 4. The dielectric material preferably comprises aluminium oxide, titanium oxide or the oxide, nitride, carbide, boride or silicide of some other suitable element, such as carbon, nitrogen, borium or silicon, or of some metal or metals or crystalline or amorphous silicate, such as glass, $SiO_2$ (e.g. quartz) or some other material lined inside with a dielectric coating or an appropriate polymer material. The polymer material must be sufficiently dense or compact to prevent a gas to be examined from passing or diffusing therethrough to any notable extent. The polymer material must also be inactive or inert relative to a gas to be examined. Also other types of minerals, such as mica, are applicable as a material for the wall 16 but the use thereof may be more problematic in terms of construction. In the present case, the measuring chamber 4 includes opposite outer surfaces 19a, 19b provided with plate-like or superficial electrodes 2 and 3. Thus, together with the electrically conductive electrodes 2, 3 spaced by a distance $H_2$ from each other, the measuring chamber creates a sort of flat stack capacitor, whose wall 16 made of an insulating material defines thereinside the measuring chamber 4 for passing therein a gas G to be analyzed. The measuring chamber 4 is supplied with a gas to be measured through an inlet connection 5 as a flow $G_1$ and the gas leaves the chamber through an outlet connection 6 as a flow $G_2$. In this case, the chamber has an external height $H_2$, i.e. the distance between electrodes 2, 3, which is preferably small, not more than approximately 3 mm and preferably in the order of 1 mm. Thus, the measuring chamber, i.e. the gas cell 4, has an internal height $H_1$ which is also small and preferably less than 1 mm. One of the resulting effects is e.g. that a high voltage U required for the excitation of molecules can be maintained quite reasonable, as can be concluded on the basis of FIG. 7.

The measuring chamber 4 includes a first end or wall section 46 having an inner surface 18' preferably made up by a mirror surface 7 which reflects a radiation developed in the chamber towards a window 8 making up a second end or wall section 47 and allowing the emission of a radiation, such as light, to be measured out of the chamber and to light detector elements 12. The window 8 must be transparent to a particular radiation, i.e. light, emitted by a gas contained in the measuring chamber 4 by the action of an electrical field. Depending on the type of light detector element mounted outside the window, the window material must also have a diffusivity which is either low for a light beam emitted from the chamber to retain its direction and strength or higher for a radiation emitted through the window to be scattered. The window 8 may be made of the same material as the rest of the chamber or, for example, of mica.

In a particularly preferred solution, the material for an inner surface 18, 18' of the measuring chamber 4 comprises a multi-layer and multi-foil mirror, i.e. an interference mirror 51, made of dielectric materials. This multi-layer mirror coating 51 preferably covers all of the inner chamber surface except a section 50 in line with the window 8 since, of course, the radiation must be able to pass therethrough. Thus, the measuring can be provided with light at very small dissipations. It is possible that such a dielectric multi-layer mirror 51 would suffice as an insulation for electrodes relative to the gas mixture G contained in the chamber 4. In this design, the electrodes would be provided on the inner surface of a mechanically supporting section of the wall 16, coated with this multi-layer mirror, and the multi-layer mirror surfaces would be assembled towards each other as a measuring chamber. It is obvious that the chamber can also be provided with a coating of another type of dielectric material on the inner surfaces 18, 18' and that the mirror 7 included in the end 46 can be a conventional metal-coated mirror mounted outside the chamber wall 16. These dielectric coating materials forming said multi-layer or interference mirror coating 51 may basically be any per se known electrically insulating materials used for such mirrors and like interference filters which are capable of withstanding the conditions existing in the measuring chamber 4. Such dielectric materials include for example $SiO_2$, $TiO_2$ and $MgF_2$, which have different indices of refraction and which are processed with known techniques for producing layers, which have a properly proportioned thickness relative to wavelengths and which, laid on top of each other in a certain per se known fashion, create a reflecting mirror surface based on the interference of light.

Figure 5A:
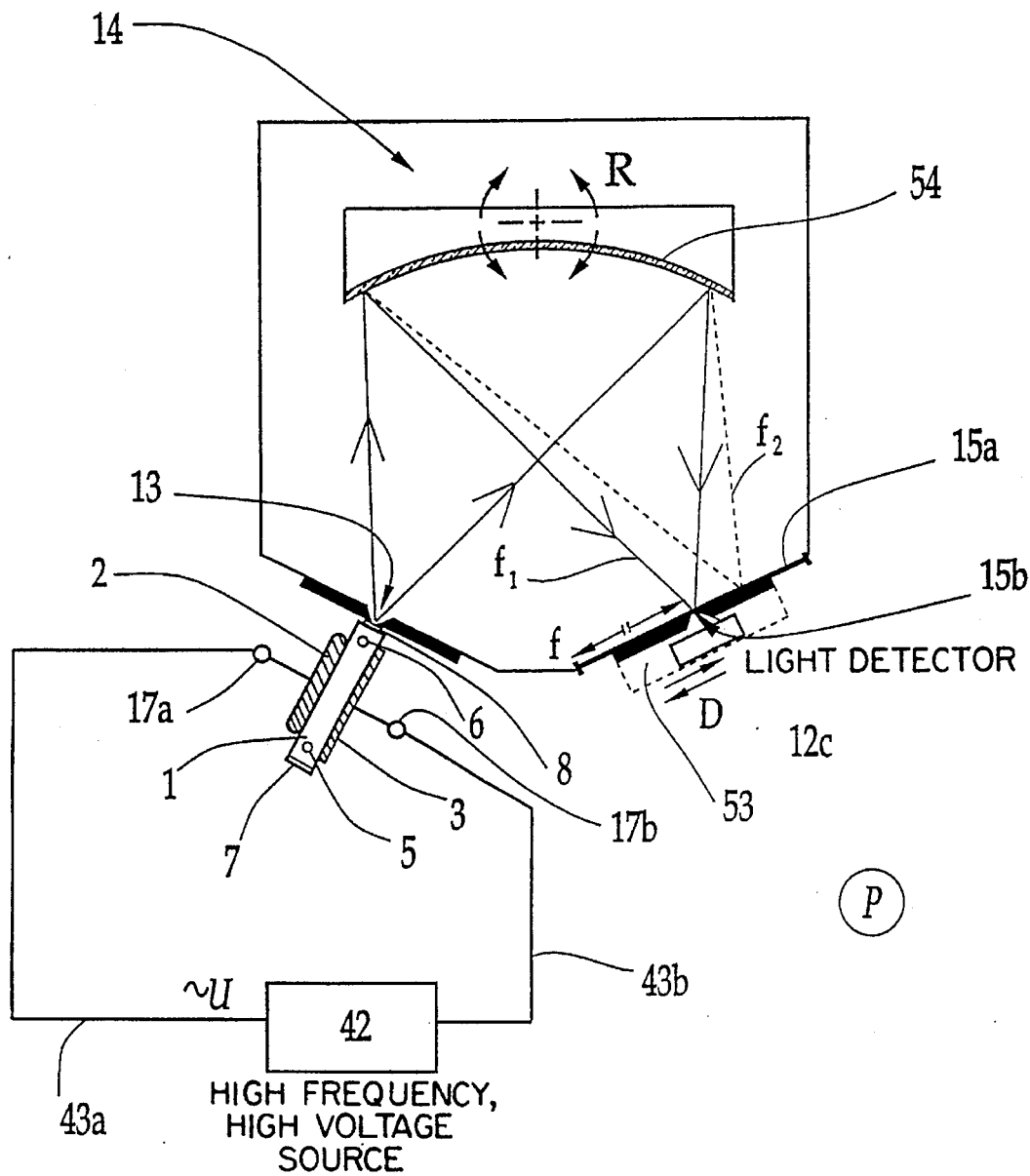
FIG. 5A shows a measuring sensor of the invention provided with a second embodiment for a light detector arrangement, including a spectrometer and two optional ways of varying a wavelength reaching the light detector.
Figure 5B:
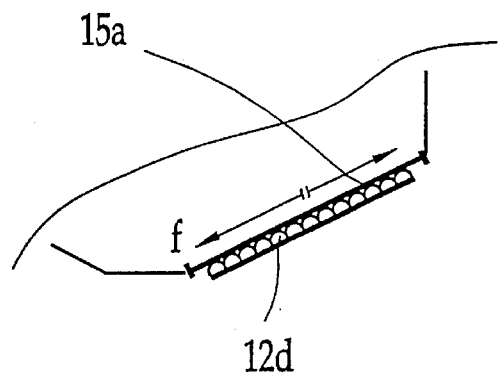
FIG. 5B shows a third embodiment for a light detector arrangement of the invention which is compatible with a spectrometer used in the measuring sensor of the invention appearing in FIG. 5A.

The chamber 4 may be small also in other dimensions, a length L and a width W, as long as no disruptive discharge is allowed to occur e.g. as a surface current between electrodes 2 and 3 past the measuring chamber. In order to enable a low sample flow rate Ft, no more than 200 ml/min, and still have a high reaction rate to concentration variations such that, even at a low sample flow rate Ft, there will be enough time for the entire gas volume contained in the chamber to be replaced, the other chamber dimensions L, W can be preferably in the order of 10 mm×10 mm. The measuring chamber 4 should have a capacity or a volume V which in practice does not exceed 5 cm$^3$ but is preferably less than 1 cm$^3$. A typical volume may be 0.1 cm$^3$ which, at the above sample flow rate, provides a reasonably high replacement rate, 33 times a second, for the gas volume. However, in order to provide a sufficient capacitance and a sufficiently great length L for emitting radiation towards the window 8, it is appropriate that the chamber length L and width W exceed at least three times, but preferably at least six times the internal chamber height $H_1$. Typically, the length and/or width are ten to twenty times the height, as in the above-described design. On the other hand, the measuring chamber width W, along with the other dimensions, has an effect not only on total intensity of radiation emission but also on the operating mode of light detector elements. In spectrometers 14 as shown in FIGS. 5A and 5B, the width W can be in the order of one fourth or even a substantially smaller fraction of the chamber length L. Thus, the chamber would be narrow and long and the radiation emitted through a window 8 included in the narrow end would be quite directional. Generally, and particularly in the embodiment of FIGS. 1A and 1B provided with two or more light detector elements 12a, 12b mounted side by side in alignment with the window, it is preferred that the ratio of the chamber length to its width be less than approximately two and typically in the order of one. However, there is nothing to suggest that the width W of chamber 4 cannot be designed to exceed its length L. The chamber 4 can also be designed in other forms than the rectangular parallelepiped shown in the figures. Thus, one, some or all of the sides of the chamber can be curved and the entire chamber can be round and flat or spherical, an ellipse or a non-rectangular prism or designed in some other way.

Figure 2:
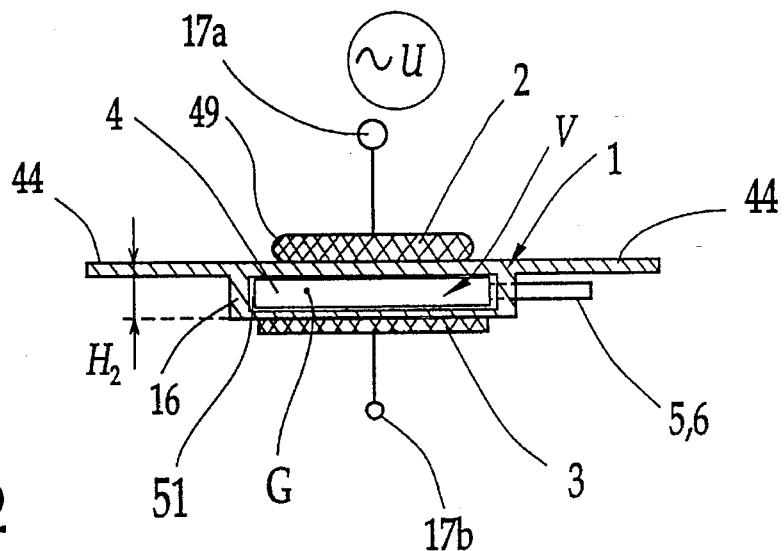
FIGS. 2–4 shows cross-sections of three other embodiments for a sensor of the invention in a view similar to FIG. 1B.
Figure 3:
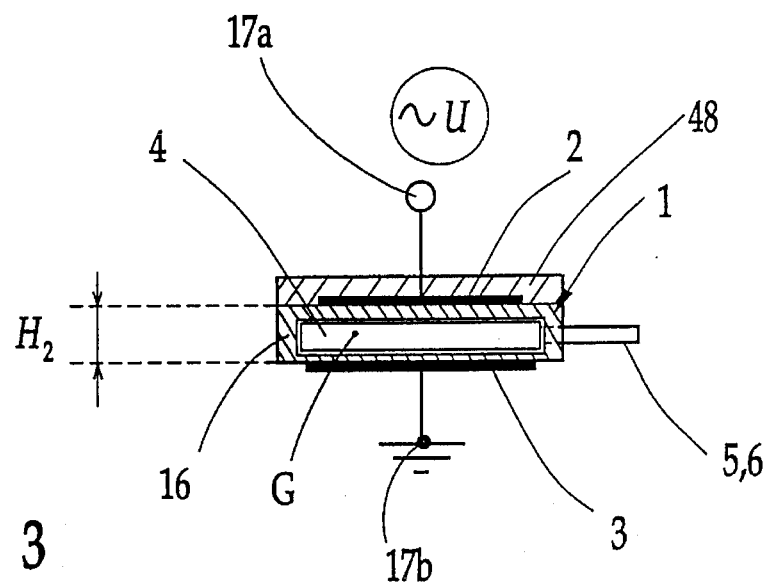
Figure 4:
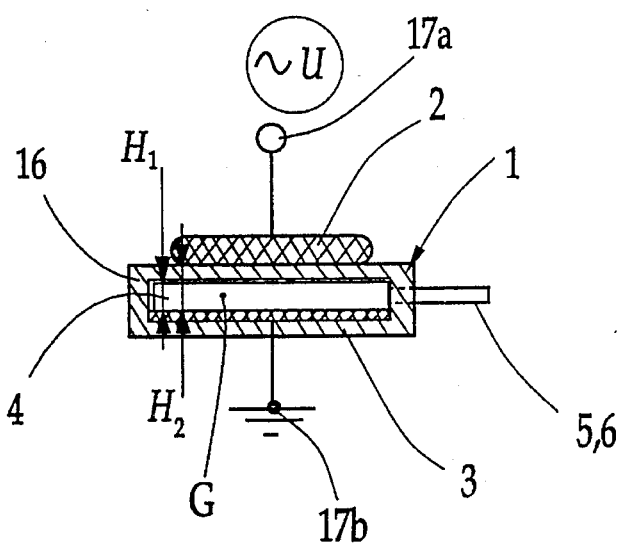

Preferably, neither of the electrically conductive electrodes 2 and 3 is in contact with the gas mixture G contained in the measuring chamber but are both located outside the electrically insulating chamber walls 16, i.e. on the outer surfaces 19a, 19b of chamber 4, as shown in FIGS. 1A, 2 and 3. It is conceivable that the second electrode 3, which is grounded by its connecting terminal 17b, could be in contact with the gas G in the chamber in cases when the measuring is effected on the sampling flow Ft separated from a main flow Fm, without causing error in the determination of concentrations. This structure is shown in FIG. 4. This structure would enable a reduction of the operating voltage U. In all alternative structures, the plate-like second electrode 3 is preferably connected with a wire 43b to the zero terminal of a voltage source 42, which is usually also grounded. To avoid the corona effect, the first electrode 2 is preferably rounded at its edges 49 and connected by its connecting terminal 17a with a wire 43a to the voltage source 42 for introducing the high-frequency high voltage U between the first and second electrodes 2 and 3. This alternating voltage can be typically about 1–5 kV, but preferably 1–2 kV, depending on the size of chamber 4 and a pressure P of the gas mixture G contained in the chamber, as can be concluded from the high rudimentary curve shown in FIG. 7. This curve describes a voltage required for the generation of an emission as a function of the product of the gas pressure existing in the chamber and a distance between the electrodes. This curve should by no means be considered conclusive or binding as it only points out the direction of voltage variation. Obviously, the voltage could be 6–8 kV or up to 10 kV, but such high voltages probably cause too much dissociation and ionization in many gas molecules. In some situations, even lower voltages, such as 500 V, can be relevant. The high voltage U has a frequency which is at least in the order of 10 kHz, preferably more than 50 kHz. The maximum limit frequency is primarily set by the restrictions of the high-voltage transformer being used and, in practice, it is about 200 kHz. No theoretical maximum value for the frequency is known.

It is believed that a rapidly alternating electrical field thus produced in the sample chamber induces the excitation of atoms or molecules contained in the chamber, yet ionizing no more than just a small portion thereof, whereby the high-frequency excitation is "soft". Thus, no plasma is obviously produced and no notable dissociation of gas molecules has been observed. Therefore, a neutral or non-ionized atom or molecule will be excited and starts emitting primarily visible light or short-range ultraviolet or infrared light. If the gas contains nitrogen molecules, it is the first or primarily the second positive system thereof that will be excited. The resulting light comprises for example a violet 406 nm wavelength included in the second positive system or the wavelengths of red light included in the first positive system. Nitrogen has been observed to have also higher-intensity wavelengths, such as 337 nm and 358 nm, as well as lower-intensity wavelengths. According to the present opinion, a wavelength providing a high intensity, such as 337 nm, affords good concentration measuring results when the measured concentrations are low, e.g. on ppm level. If it is necessary to measure slightly higher concentration readings, as in the typical embodiment of this invention, such a high intensity is no longer linear and that leads to computing problems and possible errors. Thus, it is obviously more preferable to select a wavelength, such as the 406 nm mentioned above, providing a lower intensity. For each range of nitrogen concentration, each pressure and each field strength it is possible to find a particular wavelength which affords the most linear and reliable measuring value indicating the individual nitrogen concentration reading existing in a gas mixture at any given measuring moment. Exactly the same applies also to other gases measurable by means of this sensor and method of the invention. In the measurement of low argon concentrations, it could be possible to use an intense 696 nm emission band and, in the measurement of slightly higher concentrations, an emission band of 347 nm which has a lower intensity but is more linear over the relevant range of concentration measurement (see the cited article in publication "Analytical Chemistry" vol. 34, No. 10, 1962). A preferred measuring wavelength for helium is expected to be 502 nm. A preferred emission band for xenon is probably on a 473 nm wavelength. The above values should not be considered binding but just illustrative of the principles for selecting wavelengths. For each application, for example, preliminary tests can be employed for determining which wavelength or wavelengths can be beneficially used for measuring the concentration of each gas component in order to achieve the optional measuring result. The comparison of wavelengths emitting at any given time with the known emission wavelengths of various gases can provide an identification as to which gases are contained in a mixture. In order to eliminate a disruptive discharge, the insulation of a small measuring chamber 4 can be enhanced e.g. by the solution of FIG. 2, wherein one wall of the chamber is extended by means of extensions 44 without increasing the volume V of the chamber 4. Another similar solution for the insulation of a small chamber is shown in FIG. 3. The first electrode 2 subjected to a high voltage is surrounded by an electrically insulating material 48. Since no corona effect is then allowed to occur past the chamber, the shape of electrode 2 and especially that of the edge is not critical but the electrode can be for example in the form of a metal foil on the outer sample chamber surface 19*a*. Similarly, the second electrode 3 can be a metal foil on the outer chamber surface 19*b*, which can also be surrounded by an electrically insulating material, not shown in the figures. A measuring sensor of the invention can be used for the identification and determination of the concentration of components in gas mixtures G over such a pressure range, wherein the determined electrical excitation produces a suitable radiation emission. According to current information, it seems that the measuring sensor functions at a gas-mixture pressure P, which is in the range of 0.1–10 bar. Since the air pressure at an altitude of 10 km is approximately 0.28 bar and at the depth of 50 m underwater approximately 6 bar, it can be concluded that a measuring sensor of the invention is operable at high altitudes and in spaces having a vacuum of 0.2 bar as well as under the pressurization of 6 bar everywhere a human being is functional. The most typical operating range is nevertheless a pressure equal to the normal atmospheric pressure, which can be slightly increased or decreased by the delivery of a gas mixture, i.e. a pressure range in the order of 0.5–2 bar.

The spectroscopic analysis or measuring indicates that the measuring is effected by observing emitted or absorbed wavelengths and/or the strength of emission or absorption, as generally known. A sensor of the invention discussed in this application is used for the examination of emission and, thus it is capable of carrying out both qualitative and quantitative analysis. Both analyses are effected by measuring emitted radiation by means of a light detector element and preferably over narrow wavelength bands. In the case that the radiation emitted from a measuring chamber includes or may include several emission peaks, the narrow wavelength band refers to such a wavelength range $\Delta f$, which substantially separately accommodates within the limits thereof an emission peak or each of several emission peaks to be examined but which does not accommodate within the limits thereof the other adjacent emission peaks which are possibly harmful to the analysis of the emission peak being examined. When interference filters 9*a*, 9*b*, to be discussed later in this application, or a spectrometer 14, are used this wavelength range $\Delta f$ has generally a width which is in the order of 1–100 nm and preferably in the order of 10 nm. When tradition filters 9*a*, 9*b* based on pigments are used, the wavelength ranges $\Delta f$ are considerably more extensive and vague than this, since the variations of an absorption produced by pigments upon the variation of a wavelength are typically gentle. A corresponding situation arises when utilizing for example the varying sensitivity of a detector to various wavelengths, i.e. the sensitivity distribution of a detector. In these cases, wherein the actual wavelength range cannot be defined or wherein the chamber only produces a single emission to be analyzed, the narrow wavelength band is in fact an irrelevant quantity but it can be interpreted as the width of this particular emission band.

The light produced in chamber 4 can be measured for example non-dispersively, as shown in FIG. 1, wherein light detector elements 12 are mounted in alignment with the chamber window 8 outside the chamber and optically directed towards the interior V of chamber 4. This particular case includes two light detector elements or detectors 12*a* and 12*b* which are located parallel to each other in the direction of a surface 52 included in the window 8 and the chamber width W. Between each detector 12*a* and 12*b* and the window is fitted a respective filter, having a narrow transmission band, i.e. respective bandpass filters 9*a* and 9*b*. The bandpass filters 9*a*, 9*b* are preferably prior known and commercially available interference filters. In addition, it is appropriate to locate between the chamber window 8 and the filter or filters 9*a*, 9*b* an optical collimator, such as a collimating lens 10 or collimating lenses, whereby the light emitted from the chamber can be directed in view of passing it in the form of an at least principally parallel beam of rays through the bandpass filters. It is also beneficial to locate between the filters 9*a*, 9*b* and the detectors a focusing lens or lenses 11*a* and 11*b*, whereby a beam of rays having passed through the bandpass filters is effectively focused on the relevant detector 12*a* and, respectively, 12*b*. Said filters 9*a* and 9*b* are provided with transmission bands adapted to such radiation wavelengths $f_3$ and $f_4$ which correspond to emission wavelengths desired for gas components of the gas mixture G. Thus, the detector 12*a*, along with its filter 9*a*, measures radiation intensity on one wavelength band and the second detector 12*b*, along with its filter 9*b*, measures radiation intensity on another wavelength band. If just one wavelength is being measured and/or if the filters 9 do not require collimated light and/or if the detectors 12 can be otherwise supplied with sufficient light, the arrangement can be provided with a conventional colour filter and the collimation and/or focusing can be omitted and, thus, the relevant mechanical components can be eliminated, whereby even the window 8 can possibly be somewhat diffuse. The above has described the measurement of two wavelengths but, if necessary, the window 8 can be aligned with more, such as three or four detectors, provided with relevant bandpass filters and located parallel to each other. This procedure can also be used for identifying in a simple manner a limited number of previously known gas components by setting the transmission bands of bandpass filters on the wavelengths corresponding to the emission bands thereof, whereby the reception of a signal from a detector corresponding to a given filter indicates the presence of the gas in question.

The light produced in chamber 4 can also be measured dispersively such that the chamber window 8 is designed as an inlet for a prism or grating spectrometer 14, as in FIGS. 5A, 5B. The spectrometer 14 is provided with an inlet slit 13 for optically aligning the chamber window 8 therewith in such a manner that radiation emitted from the chamber passes inside the spectrometer as intended and comes into contact e.g. with a grating 54 and further, dispersed in wavelengths, arrives in an exit zone 15*a*. The spectrometer 14 includes an exit zone 15*a* and directed towards that zone is a generated spectrum f consisting of various wavelengths set side by side. The spectrometer of FIG. 5A is provided in this exit zone 15*a* with an outlet slit 15*b* upstream of a light detector element or detector 12*c* and, thus, it serves as a monochromator for measuring one wavelength, such as $f_1$ and $f_2$, at a time. In view of selecting a given desired wavelength, the outlet slit 15*b* and the detector 12*c* are displaceable as a single assembly 53 within the exit zone 15*a* in its direction D. Optionally, it is possible to maintain the assembly 53 formed by outlet slit 15b and detector 12c stationary within the exit zone 15a and, instead, to rotate the grating 54 or respectively the prism in directions R, whereby the wavelength coming to contact with the detector 12c changes as above. Both of these above-described embodiments, a displacement in directions D or a displacement in directions R, are shown in FIG. 5A, however, they are actually alternative features which in practice do not appear simultaneously in one device. Instead of an outlet slit and a single detector, an alternative arrangement comprises within the exit zone 15a a sequence of detectors 12d or a CCD detector, as shown in FIG. 5B, wherein the light-sensitive elements are side by side in the direction of a spectrum f for measuring simultaneously an entire spectral range or a plurality of narrow spectral ranges. However, the solution shown in FIGS. 1A, 1B is the most preferable for measuring just one or two wavelengths or a few wavelengths, as shown in the figure. One filter-detector couple 9, 12 may serve for example as a reference, if a suitable wavelength for such an optical reference is found, while the other measures the emission of a target gas. Especially these embodiments of the invention operating with the help of a spectrometer can be used for the identification of gas components particularly in cases where the components may vary or be unknown, since the detector 12c or detectors 12d are capable of the precise verification of emitted wavelengths, e.g. by scanning mechanically or electrically across the entire wavelength range. Since each gas is provided with quite specific emitted wavelengths, the gas components are distinctly verifiable.

The above-discussed optical alignment or focusing of light detector elements 12 and respectively a spectrometer 14 towards the interior V of a chamber 4 includes both a direct focusing and an indirect focusing, effected by way of a mirror or mirrors, or a like feature. One possibility is also to employ an optical fiber or a bundle of fibers, e.g. "fiber optics", between the chamber window 8 and the collimating lens 10 or respectively between the window and the inlet slit 13 of spectrometer 14, whereby the light detector elements can be located very flexibly relative to the chamber. The useful detectors or light detectors 12a, 12b, 12c and 12d may preferably include for example a silicon detector, an indium-gallium-arsenide detector or a photo-multiplier tube but any other per se known and commercially available detector, which is sufficiently sensitive to an applied wavelength, can be used.

Figure 6:
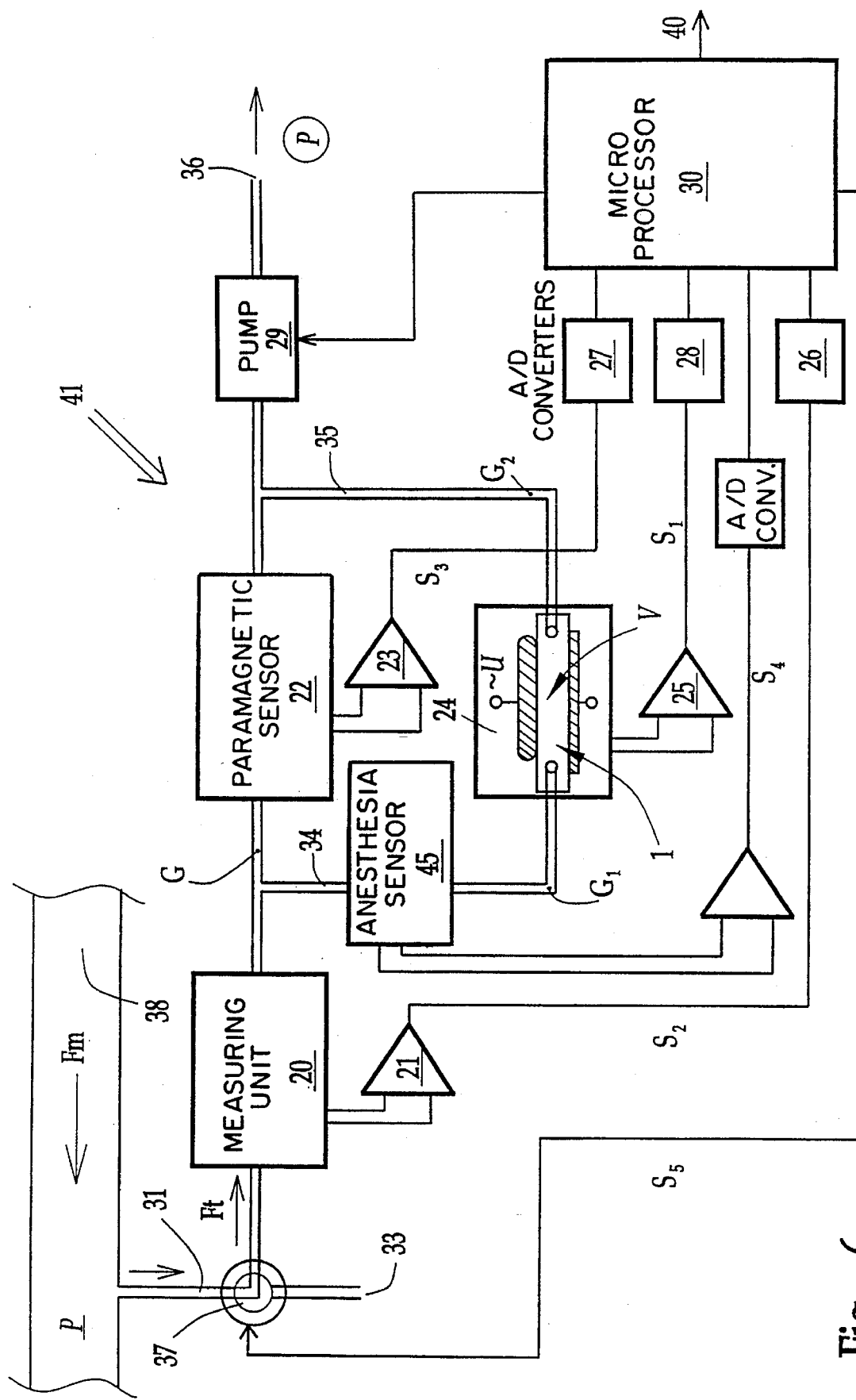
FIG. 6 shows schematically a measuring arrangement which includes a measuring sensor of the invention for determining the concentration of a plurality of gas components included in a gas mixture.

The best way to compensate for interferences caused in the excitation of a target gas by possible gas components other than those actually subjected to measuring is to measure such gases separately and, if possible, with different methods. In a patient monitor, for example, carbon dioxide, laughing gas and anesthesia gases are normally measured by the application of infrared absorption technique and oxygen by means of a paramagnetic sensor. Oxygen and carbon dioxide, as such, do not have an interfering emission in the above-described measuring sensor of the invention but, when present in the same gas mixture, these molecules may, in the relative collisions of gas molecules, transfer some of the latent excitation energy thereof directly to nitrogen molecules and thereby affect the excitation efficiency of nitrogen and the intensity of emitted radiation. An arrangement of the invention applicable to multi-gas measuring is illustrated in FIG. 6.

A measuring arrangement 41 comprises a measuring sensor 1 of the invention and a circuit preferably associated therewith, not shown in the figures and producing a high-frequency high voltage U and light detector elements 12 along with its auxiliary equipment 9 or 14, as well as its electronics partially included in a housing 24. A duct 38 carries a main flow Fm, bringing a gas mixture G to the site of the intended application. This main flow can be e.g. a flow traveling in the tube system of a respirator. From this main flow is aspirated a sample flow Ft by means of a pump 29 into a tube 31. The sample progresses for example through a valve 37 preferably first to a measuring unit 20 operated by an infrared-absorption sensor and further through this infrared-absorption sensor into a measuring chamber 4, which is in series with the sampling flow and included in the measuring sensor 1 of the invention. The infrared sensor 20 can be of any appropriate structural design, such as a type described in the publication U.S. Pat. No. 4,233,513 or any other known type. In addition, the arrangement comprises a sensor 22, which uses the paramagnetic phenomenon and which in this embodiment is connected in parallel with the measuring sensor 1 of the invention relative to the sampling flow Ft. This paramagnetic sensor 22 can be of any appropriate design, such as a type preferably described in the publication U.S. Pat. No. 4,633,705. Occasionally, the sensor 22 uses ambient air as a reference, which could interfere with the measurement of nitrogen, otherwise the connection in series would be possible. On the other hand, the infrared sensor 20 is in this case positioned first in the flow Ft since, in anesthesia application, it measures e.g. carbon dioxide concentration and the speedy discovery of this is most important. In other applications, of course, the sensors can be of another type and the sensors can be positioned in another sequence. Often, especially in anesthesia application, the arrangement further includes a sensor 45 for the identification of anesthesia gases and that can be preferably of the type described in the publication U.S. Pat. No. 5,070,245. A signal produced by this sensor is designated at $S_4$.

Each sensor 1, 20, 22 is normally provided with its own per se known preamplifier 25, 21 and 23, respectively, as well as with its own analogue-digital converter 28, 26 and 27, respectively, through which electrical signals $S_1$, $S_2$ and $S_3$, respectively, received from the sensors are provided to a computing unit, such as a microprocessor 30. Thus, the computing unit 30 collects the measuring signals $S_1$, $S_2$ and $S_3$ from each sensor and performs possible comparisons of the measuring values as well as necessary corrections to the concentration values and/or identification values obtained from the original measuring signals. The final corrected values are sent by the computing unit 30 along a path 40 to a display, a storage unit or a like, not shown. Possible correction or rectification calculations are effected by the computing unit 30 according to the predetermined calculation rules, which may be based on test runs effected on various gas mixtures. It is to be expected that the signals $S_2$ and $S_3$ received from sensors 20 and/or 22 must be used for correcting the concentrations determined by means of the signal $S_1$ received from sensor 1. However, it is possible that there is no need to make essential corrections or rectifications or that corrections must be made in a different order.

Thus, the measuring arrangement 41 of the invention is capable of checking and, if necessary, correcting a concentration calculated on the basis of a signal $S_1$, $S_2$ and $S_3$ produced by any of the sensors by means of any other second measuring signal or signals $S_1$–$S_3$. This checking may be based either on the fact that different sensors measure the same gas component whenever it is possible or on the fact that the concentration of remaining gas components is calculable by means of the concentrations of determined gas components. Other approaches are also conceivable. These potentially required correction rules or algorithms or the like must only be programmed in a microprocessor included in the computing unit 30. On the basis of signals $S_1$, $S_2$ and $S_3$, it is of course also possible to output directly the analysis results produced by the relevant sensors 1, 20, 22 as measuring values, such as the identification and/or concentration of gas components, for producing the analysis results of several gas components. In this case, a measuring arrangement of the invention may include a plurality of computing units, for example one for each sensor. The not shown display equipment and storage units can be common or separate, depending on a particular application.

A portion picked up from the main flow Fm into the sample flow Ft is so small that its volume flow rate does not affect the main flow. Thus, a portion picked up from the main flow is not more than 20% and preferably not more than about 10%, but even considerably smaller amounts, such as one percent or less, can be used depending of course on the volume of the main flow. In an anesthesia related application, the infrared-absorption sensor 20 is used for measuring at least carbon dioxide as well as laughing gas, the paramagnetic sensor 22 for oxygen, and the spectroscopic sensor 1 based on a silent electrical discharge is used for nitrogen and possible helium and argon. From the pump 29, said gas sample flow Ft emerges through a tube 36 for example to ambient air. Simple calibration of nitrogen can be effected by aspirating ambient air 33 into the chamber 4 of sensor 1 through a second branch 33 included in the valve 37. Since air contains about 78% of nitrogen, the reference point can be set. This type of resetting or zeroing is also included in the operating routines of sensors 20 and 22 and is performed by means of a common automatic command signal $S_5$ produced e.g. by the computing unit. The sensor 1 is preferably sealed in a light tight housing 24, so that the zero point of a measuring signal would not depend on external light sources, although the operating frequency of a light detector element and its electronics could also be adapted to the frequency of said high voltage U delivered to the electrodes of chamber 4 and exciting said gas G in view of minimizing the effect of external light. In the same insulated housing can also be sealed a high-voltage transformer and electronics associated therewith, whereby the sensor is of a low voltage externally and hence perfectly safe.

Thus, when analyzing a gas mixture is analyzed by means of a sensor of the invention, the result will be the determination of various measuring values which include e.g. emitted wavelength as well as emitted radiation intensity. These can be used for both identifying the relevant gas components included in said mixture as well as the concentrations thereof. A measuring arrangement of the invention including a plurality of sensors is capable of analyzing all relevant gas components included in a gas mixture as well as checking and, if necessary, correcting both the obtained identification values and the obtained concentration values of gas components. The above description deals with preferred embodiments of the invention but the invention is not limited thereby and can be modified and varied within the scope of the appended claims.

I claim:

1. A measuring sensor for the spectroscopic analysis of gas mixtures by means of a silent electrical discharge, the measuring sensor (1) comprising:
   a chamber (4) which includes a wall (16) made primarily of a dielectric material and surrounding the chamber; through-going flow connections (5,6) in the wall for passing a gas mixture to be analyzed into ($G_1$) and out of ($G_2$) the chamber; first and second electrodes (2,3) on the opposite sides of the chamber with a high alternating voltage (U) applied therebetween; and at least one window (8) included in the wall and transmissive to wavelengths to be measured; and
   at least one radiation detector element (12) positioned for measuring the intensity of radiation emitted through said window,
   said high alternating voltage (U) having a frequency which is at least on the order of 10 kHz for producing a radiation emission based on the soft, substantially non-ionizing excitation of molecules and/or atoms in a gas mixture (G) to be analyzed and contained in the chamber (4).

2. A measuring sensor as set forth in claim 1, characterized in that the electrodes (2,3) have applied thereto a high alternating voltage (U) having a frequency which is more than about 50 kHz and having a potential which is between 0.5–10 kV, and that said first and second electrodes (2,3) are located opposite to each other on outer chamber surfaces (19a, 19b), and are not in contact with the gas mixture (G) in said chamber (4).

3. A measuring sensor as set forth in claim 1, characterized in that the chamber contains the gas mixture (G) to be measured at a pressure (P) which is between about 0.1–10 bar.

4. A measuring sensor as set forth in claim 1, characterized in that the chamber (4) has an internal length (L) and a width (W) which are at least three times the internal chamber thickness ($H_1$), that the ratio of said chamber length (L) to the width (W) is not more than about four, and that the chamber has a volume (V) which is less than about 5 cm$^3$, whereby the electrodes (2,3) on the opposite surfaces of the chamber have an arcing distance ($H_2$) which is not more than about 3 mm.

5. A measuring sensor as set forth in claim 1, characterized in that the wall (16) of said chamber (4) is comprised of one of crystalline or amorphous silicate, a metallic oxide, and a chemically inert polymer which has a low gas diffusion, and that at least a wall section (18') opposite to the window (8) includes a mirror (7) for directing the emitted radiation developed in the gas mixture of said chamber towards the window.

6. A measuring sensor as set forth in claim 1, characterized in that, with the exception of a section (50) aligned with the window (8), the inner surface (18, 18') of the chamber (4) is at least partially coated with a multi-layer interference mirror surface (51) made of dielectric materials.

7. A measuring sensor as set forth in claim 1, characterized in that between said radiation detector element (12) and the chamber window (8) is fitted an optical filter (9) provided with a narrow transmission band for measuring the emitted radiation in narrow wavelength bands, and that between the chamber window (8) and the filter is a collimator (10) and between the filter and the radiation detector element is a focusing lens (11).

8. A measuring sensor as set forth in claim 1, characterized in that in alignment with the chamber window (8) and parallel to each other in the direction of a window surface (52) there are two or more radiation detector elements (12a and 12b) and between each of such radiation detector elements and the window (8) is fitted an optical filter (9a and 9b) provided with a narrow transmission band, whereby the transmission band of each of the different filters is on a different wavelength ($f_3$, $f_4$) for identifying the intensity of various radiation bands included in the emission occurring in the gas mixture (G).

9. A measuring sensor as set forth in claim 1, characterized in that between a radiation detector element (12c) and the chamber window (8) is fitted a spectrometer (14) provided with a radiation inlet slit (13) and a radiation exit zone (15a), that the chamber window is positioned in alignment with the inlet slit in such a manner that the emitted radiation leaving the chamber (4) passes through the inlet slit (13) into the spectrometer, and that the exit zone (15a) is provided with an outlet slit (15b) and in alignment therewith said radiation detector element (12c), said outlet slit and said radiation detector element being displaceable (D) within the exit zone as a single assembly for measuring various wavelengths of the emitted radiation in narrow wavelength bands.

10. A measuring sensor as set forth in claim 5, characterized in that, with the exception of section (50) aligned with the window (8), the inner surface (18, 18') of the chamber (4) is at least partially coated with a multi-layer interference mirror surface (51) made of dielectric materials.

11. A measuring sensor as set forth in claim 7, characterized in that in alignment with the chamber window (8) and parallel to each other in the direction of a window surface (52) there are two or more radiation detector elements (12a and 12b) and between each of such radiation detector elements and the window (8) is fitted an optical filter (9a and 9b) provided with a narrow transmission band, whereby the transmission band of each of the filters is on a different wavelength ($f_3$, $f_4$) for identifying the intensity of various radiation bands included in the emission occurring in the gas mixture.

12. A measuring sensor as set forth in claim 1 characterized in that the electrodes (2,3) have applied thereto a high alternating voltage (U) having a frequency which is more than about 50 kHz and a potential which is between 0.5–10 kV, and that said first electrode (2) is located on an outer chamber surface (19a) and the second electrode (3) has a zero potential and is located on an inner surface (18) included in the wall (16) of said chamber (4) so as to be in contact with the gas mixture (G) in the chamber.

13. A measuring sensor as set forth in claim 2 characterized in that the electrodes (2,3) have applied thereto a high alternating voltage (U) having a potential between 1–5 kV.

14. A measuring sensor as set forth in claim 13 characterized in that the electrodes (2,3) have applied thereto a high alternating voltage (U) having a potential between 1–2 kV.

15. A measuring sensor as set forth in claim 12 characterized in that the electrodes (2,3) have applied thereto a high alternating voltage (U) having a potential between 1–5 kV.

16. A measuring sensor as set forth in claim 15 characterized in that the electrodes (2,3) having applied thereto a high alternating voltage (U) having a potential between 1–2 kV.

17. A measuring sensor as set forth in claim 3, characterized in that the chamber contains the gas mixture (G) to be measured at a pressure (P) which is between about 0.2–6 bar.

18. A measuring sensor as set forth in claim 17, characterized in that the chamber contains the gas mixture (G) to be measured at a pressure (P) which is between about 0.5–2 bar.

19. A measuring sensor as set forth in claim 4, characterized in that the chamber (4) has an internal length (L) and a width (W) which are at least six times the internal chamber thickness ($H_1$), that the ratio of said chamber length (L) to the width (W) is less than two, and that the chamber has a volume (V) which is less than 1 cm$^3$.

20. A measuring sensor as set forth in claim 19, characterized in that the chamber (4) has an internal length (L) and a width (W) which are ten to twenty times the internal chamber thickness ($H_1$), that the ratio of said chamber length (L) to the width (W) is on the order of one, and that the chamber has a volume (V) on the order of 0.1 cm$^3$, whereby the electrodes (2,3) on the opposite surfaces of the chamber have an arcing distance ($H_2$) which is on the order of 1 mm.

21. A measuring sensor as set forth in claim 1, characterized in that the chamber window (8) of said chamber (4) is comprised of one of crystalline or amorphous silicate, a metallic oxide, a chemically inert polymer having a low gas diffusion, and mica.

22. A measuring sensor as set forth in claim 7, wherein the optical filter is an interference filter.

23. A measuring sensor as set forth in claim 8 wherein the optical filter comprises an interference filter.

24. A measuring sensor as set forth in claim 9, wherein said spectrometer (14) is one of a prism and a grating spectrometer.

25. A measuring sensor as set forth in claim 1, characterized in that between a radiation detector element (12c) and the chamber window (8) is fitted a spectrometer (14) provided with a radiation inlet slit (13) and a radiation exit zone (15a), said spectrometer having one of a grating (54) and a prism, that the chamber window is positioned in alignment with the inlet slit in such a manner that the emitted radiation leaving the chamber (4) passes through the inlet slit (13) into the spectrometer, and that the exit zone (15a) is provided with an outlet slit (15b) and in alignment therewith said radiation detector element (12c), said grating or prism included in the spectrometer being rotatable (R) relative to the exit zone for focusing various wavelengths ($f_1$, $f_2$) on the radiation detector element (12c) for measuring various wavelengths of emitted radiation in narrow wavelength bands.

26. A measuring sensor as set forth in claim 1, characterized as including a spectrometer (14) provided with a radiation inlet slit (13) and a radiation exit zone (15a), that the chamber window is positioned in alignment with the inlet slit in such a manner that the emitted radiation leaving the chamber (4) passes through the inlet slit (13) into the spectrometer, and that the exit zone (15a) is provided with two or more radiation detector elements parallel to each other in the direction of a spectrum (f) to form a radiation detector assembly (12d) for measuring various wavelengths of the emitted radiation in narrow wavelength bands.

27. A measuring sensor as set forth in claim 26, wherein said spectrometer (14) is one of a prism and a grating spectrometer.

28. A measuring sensor as set forth in claim 11, wherein the optical filter is an interference filter.

29. A measuring sensor as set forth in claim 1, characterized in that the chamber contains the gas mixture (G) to be measured at a pressur (P) approximately equal to that of ambient air.

* * * * *